(12) United States Patent
Ziegelhoffer et al.

(10) Patent No.: US 7,745,698 B2
(45) Date of Patent: Jun. 29, 2010

(54) PEPTIDE EXTENSION FOR ENHANCEMENT OF TRANSGENE EXPRESSION IN CHLOROPLASTS

(75) Inventors: Thomas Ziegelhoffer, Madison, WI (US); Sandra Austin-Phillips, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 206 days.

(21) Appl. No.: 11/600,566

(22) Filed: Nov. 16, 2006

(65) Prior Publication Data

US 2008/0120738 A1 May 22, 2008

(51) Int. Cl.
*C12N 15/82* (2006.01)
(52) U.S. Cl. .................. 800/298; 435/320.1; 424/93.2; 800/278; 800/284
(58) Field of Classification Search .................. None
See application file for complete search history.

(56) References Cited

U.S. PATENT DOCUMENTS

| | | | |
|---|---|---|---|
| 5,451,513 A | 9/1995 | Maliga et al. | |
| 5,545,817 A | 8/1996 | McBride et al. | |
| 5,545,818 A | 8/1996 | McBride et al. | |
| 5,614,395 A | 3/1997 | Ryals et al. | |
| 5,877,402 A * | 3/1999 | Maliga et al. | 800/298 |
| 5,981,835 A | 11/1999 | Austin-Phillips et al. | |
| 6,297,054 B1 * | 10/2001 | Maliga et al. | 435/468 |
| 6,818,803 B1 | 11/2004 | Austin-Phillips et al. | |
| 2002/0062502 A1 | 5/2002 | Lebel et al. | |

FOREIGN PATENT DOCUMENTS

| | | |
|---|---|---|
| WO | WO 96/27673 | 9/1996 |
| WO | WO 97/13864 | 4/1997 |

OTHER PUBLICATIONS

Adams S.P. et al., "Hindered Dialkylamino Nucleoside Phosphite Reagents in the Synthesis of Two DNA 51-Mers," *J. Am. Chem. Soc.*, 105: 661-663 (1983).
Ausubel et al., Current Protocols in Molecular Biology, vols. 1-3, John Wiley & Sons, Inc. (1993).
Bartlett J.M.S., Stirling D., eds., PCR Protocols: Methods in Molecular Biology, second ed., Humana Press, Totowa, New Jersey (2003).
Bock and Khan, "Taming plastids for a green future," *Trends in Biotechnology*, 22(6): 311-318 (2004).
Britt and May, "Re-engineering plant gene targeting," Trends in Plant Science, 8(2): 90-95 (2003).
Fulton et al., "Microprep Protocol for Extraction of DNA from Tomato and other Herbaceous Plants," *Plant Mol. Biol. Rep.*, 13: 207-209 (1995).
Gatz, C., "Chemical Control of Gene Expression", *Annu. Rev. Plant Physiol Plant Mol. Biol.*, 48: 89-108 (1997).
Goldschmidt-Clermont M., "Transgenic expression of aminoglycoside adenine transferase in the chloroplast: a selectrable marker for site-directed transformation of chlamydomonas," *Nucl. Acids Res.* 19(15): 4083-4089 (1991).
Kim J. et al., "Ribosomes Pause at Specific Sites during Synthesis of Membrane-bound Chloroplast Reaction Center Protein Di*," *J. Biol. Chem.*, 266: 14931-14938 (2001).
Kriegler, Gene transfer and expression: A laboratory manual, Stockton Press, New York (1990).
Lessard P.A. et al., "Manipulating Gene Expression for the Metabolic Engineering of Plants," *Metabolic Engineering*, 4: 67-79 (2002).
McBride et al., "Controlled expression of plastid transgenes in plants based on a nuclear DNA-encoded and plastid-targeted T7 RNA polymerase," *Proc. Natl. Acad. Sci. USA*, 91: 7301-7305 (1994).
Morton B.R., "Selection on the Codon Bias of Chloroplast and Cyanelle Genes in Different Plant and Algal Lineages," *J. Mol. Evol.*, 46: 449-459 (1998).
Sambrook et al., Molecular Cloning—A Laboratory Manual, Cold Spring Harbor Laboratory, Cold Spring Harbor, New York (1989).
Segal D.J. et al., "Zinc fingers and a green thumb: manipulating gene expression in plants," *Curr. Opin. Plant Biol.*, 6: 163-168 (2003).
Staub J.M. et al., "High-yield production of a human therapeutic protein in tobacco chloroplasts," Nature Biotechnol, 18: 333-338 (2000).
Staub J. M., and Maliga P., "Long Regions of Homologous DNA Are Incorporated into the Tobacco Plastid Genome by Transformation," Plant Cell, 4: 39-45 (1992).
Staub J. M. And Maliga P., "Accumulation of D1 polypeptide in tobacco plastids is regulated via the untranslated region of the psbA mRNA," *EMBO J.*, 12(2): 601-606 (1993).
Svab Z. et al., "Stable transformation of plastids in higher plants," *Proc. Natl. Acad. Sci. USA*, 87: 8526-8530 (1990).
Svab Z. and Maliga P., High-frequency plastid transformation in tobacco by selection for a chimeric *aad*A gene, *Proc. Natl. Acad. Sci. USA*, 90: 913-917 (1993).
K. Yoshida and A. Shinmyo, "Transgene Expression Systems in Plant, a Natural Bioreactor," J. Bioscience and Bioengineering 90(4): 353-362 (2000).
Ziegelhoffer et al., "Dramatic effects of truncation and sub-cellular targeting on the accumulation of recombinant microbial cellulose in tobacco," *Mol. Breeding*, 8: 147-158 (2001).
Ziegelhoffer, "Expression of *Acidothermus cellulolyticus* E1 endo-β-1,4-glucanase catalytic domain in transplastomic tobacco," *Plant Biotechnology Journal*, 7:527-536 (2009).

\* cited by examiner

*Primary Examiner*—Anne R Kubelik

(57) ABSTRACT

The invention provides a novel method of controlling gene expression in plastids, using a peptide extension that can be fused to a desired protein, expression cassettes that include the genetic constructs, and plants comprising the novel expression systems. A nucleic acid sequence encoding a peptide extension fused in frame to a protein coding sequence. This genetic construct is subsequently inserted into the chloroplast genome, where the peptide extension increases expression of the fused protein. The present invention further describes the use of this method for increased production of cellulose-degrading enzymes in chloroplasts.

23 Claims, 1 Drawing Sheet

US 7,745,698 B2

PEPTIDE EXTENSION FOR ENHANCEMENT OF TRANSGENE EXPRESSION IN CHLOROPLASTS

GOVERNMENT INTERESTS

The development of the present invention was supported by USDA/ARS project funds. The U.S. Government may have certain rights in the invention described herein.

TECHNICAL FIELD

This invention relates to the control of gene expression in transgenic plastids and to transgenic plants capable of expressing desired proteins. In particular, the invention provides compositions and methods for modifying the chloroplast genome to allow for increased expression of desired proteins, such as cellulose-degrading enzymes.

BACKGROUND

Most industrial enzymes are currently produced by microorganisms via large-scale fermentation. Another approach to the production of such enzymes is to express and recover these enzymes from transgenic plants. Published work in this field has increased dramatically in recent years and several agricultural biotechnology companies have initiated research into using plants as "chemical factories" for the production of industrially useful proteins including pharmaceuticals. The appeal of this technology is the capability to produce large amounts of proteins as a value added product using conventional agricultural practices, and in an environmentally friendly manner. Indeed, high value proteins have been expressed in crop plants at commercially viable levels. Relatively low-value enzymes are more challenging to produce economically in plants but enzyme production costs can usually be offset somewhat by the lower degree of purity generally required.

Plastid transformation was first described in 1988, in the unicellular alga *Chlamydomonas reinhardtii*. Since then, plastids of various higher plants have been transformed, including tobacco, *Arabidopsis*, potato, rice, tomato, cotton, and carrot. Foreign DNA is generally introduced into plastids via microprojectile bombardment, although methods relying upon polyethylene glycol and microinjection have also been developed. The introduced DNA is flanked by regions of extensive homology to the integration site, facilitating recombination with the plastid genomic target site. In this respect, plastid transformation is fundamentally different from nuclear transformation methods, in which the transgene is inserted randomly into the nuclear genome. Another fundamental difference between the two transformation systems is the presence of many copies of the chloroplast genome (up to 10,000) per cell.

Transgenic chloroplasts offer a number of advantages over conventional transgenic plants. Among the primary advantages are high levels of transgene expression and foreign protein accumulation. Compared to nuclear transformation, where levels of recombinant protein expression in excess of 1% total soluble protein are relatively rare, plastid transformation frequently yields recombinant protein levels of 1-10%. This property has been exploited to produce high levels of heterologous proteins, e.g., human somatotropin in transplastomic tobacco plants (Staub J M et al., 2000, *Nature Biotechnol* 18: 333-338). Another advantage of this mode of plant transformation is that chloroplasts are generally not present in pollen (*Medicago* sp., *Pinus* sp., are exceptions to this rule), so that genetically engineered chloroplasts are less likely to spread into unmodified plants via cross-pollination.

Agro-based resources known as lignocellulosics are plant resources that contain cellulose, hemicelluloses, and lignin. Lignocellulosics include wood, agricultural residues, water plants, grasses, and other plant substances. Lignocellulosics such as agricultural and forestry wastes and crops produced specifically for biomass offer tremendous potential as a raw material for the production of fuel and chemical feed stocks.

Cellulose and hemicellulose are the principal sources of fermentable sugars in lignocellulosic feedstocks. A major challenge in utilization of this material is the conversion of polymeric cellulose to fermentable sugars. Acid hydrolysis is a relatively cheap process but yields of sugars are low. Enzymatic breakdown with cellulases (enzymes that break down cellulose to its simple sugar components) results in higher yields but is more costly, with enzyme production as the largest single component cost.

In an effort to lower the cost of cellulose production, it is desirable to produce cellulolytic enzymes in transgenic plants (U.S. Pat. Nos. 5,981,835; 6,818,803; U.S. patent application Pub. No. US2002/0062502 A1). Methods similar to these should further be explored. It would be beneficial to develop genetically engineered crop plants that produce economically viable levels of cellulases, and to develop the technology required to use these enzymes for biomass conversion.

The development of chloroplast transformation systems for crop plants and the high protein expression levels obtained with these systems suggests that chloroplast transformation may be a preferable way to achieve high expression levels of proteins. Such expression systems could make plant-based cellulase production economically viable. The invention described herein addresses this and other related needs.

SUMMARY OF THE INVENTION

In one aspect of the invention, a nucleic acid sequence encoding a peptide extension is fused in frame to a downstream protein coding sequence. This fusion protein is then inserted into the chloroplast genome, wherein the peptide extension increases the expression of the fused protein.

In one aspect of the present invention, sequences encoding the amino-terminus (N-terminus) of PsbA (D1), a photosystem II subunit (reaction centre core protein), are fused to sequences encoding desired proteins. These fusions (genetic constructs) are then introduced into the plastid genome. In one embodiment, a 30-nucleotide sequence, encoding the first 10 amino acids, based on the DNA sequence encoding the amino-terminus of the photosystem A (psbA) gene of *Medicago sativa*, is used in a protein fusion construct. Fused to a gene of interest that encodes a desired protein, the peptide extension confers increased expression of the desired protein in the chloroplast.

In one aspect, the present invention provides a novel method of controlling gene expression in plastids, using a peptide extension that can be fused to a desired protein. The invention provides expression cassettes that include the fusion constructs (genetic constructs), and provides plants comprising the novel expression systems. In some embodiments of the invention, sequences encoding cellulose-degrading enzymes are fused to the nucleotide sequence encoding the peptide extension. The invention further describes the production of cellulose-degrading enzymes in plants via the application of genetic engineering techniques.

Also disclosed are methods of increasing heterologous protein expression in a cell or a transgenic plant. Genetic constructs, recombinant expression cassettes, DNA fusions, polynucleotides, polypeptides, proteins, and vectors for use in conjunction with the methods to increase exogenous protein expression in plants are also disclosed. The genetic constructs generally include DNA encoding the amino-terminus of the PsbA protein, fused to a DNA encoding the desired heterologous protein. Additionally disclosed are plant lines transformed with the described constructs.

In a further aspect, the invention concerns methods for enhanced production of cellulose-degrading enzymes in plants. The methods include introducing a genetic construct containing nucleic acids that encodes an N-terminus PsbA peptide extension and a cellulase. The genetic construct that encodes the fusion protein or polypeptide is then expressed in chloroplasts. The transformation of chloroplasts with the genetic construct results in synthesis of relatively high levels of cellulase in the chloroplasts.

The present invention finds utility in any industrial process requiring a plentiful supply of proteins. In particular, the invention finds utility in production of cellulases, which may be utilized for conversion of cellulosic biomass to ethanol.

DETAILED DESCRIPTION OF THE PREFERRED EMBODIMENTS

General Overview

Figure 1:
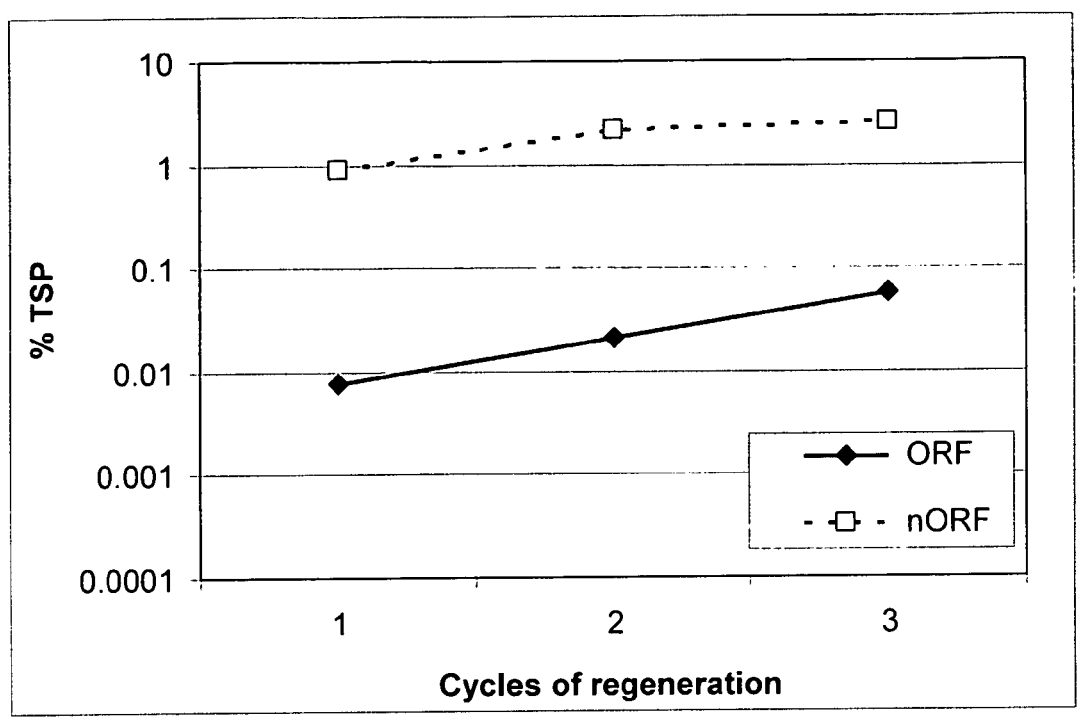
FIG. 1 is a graph depicting the percent of total soluble protein (% TSP) produced in transplastomic tobacco. A detailed description is given in the Examples section.

As used herein, the phrase "nucleic acid" or "polynucleotide sequence" refers to a single or double-stranded polymer of deoxyribonucleotide or ribonucleotide bases read from the 5' to the 3' end. Nucleic acids may also include modified nucleotides that permit correct read-through by a polymerase and do not alter expression of a polypeptide encoded by that nucleic acid.

The phrase "nucleic acid sequence encoding" refers to a nucleic acid which directs the expression of a specific protein or peptide. The nucleic acid sequences include both the DNA strand sequence that is transcribed into RNA and the RNA sequence that is translated into protein. The nucleic acid sequences include both the full length nucleic acid sequences as well as non-full length sequences derived from the full length sequences. It should be further understood that the sequence includes the degenerate codons of the native sequence or sequences which may be introduced to provide codon preference in a specific host cell.

A "coding sequence" or "coding region" refers to a nucleic acid molecule having sequence information necessary to produce a gene product, when the sequence is expressed.

The term "protein" or "polypeptide" refers to a chain of amino acids that are joined by amide bonds, also known as peptide bonds. The term "peptide" refers to a shorter string of amino acids, usually less than 50 amino acids in length. Thus, peptides differ from proteins by virtue of their size.

The term "operably linked" or "operably inserted" means that the regulatory sequences necessary for expression of the coding sequence are placed in a nucleic acid molecule in the appropriate positions relative to the coding sequence so as to enable expression of the coding sequence. This same definition is sometimes applied to the arrangement of other transcription control elements (e.g. enhancers) in an expression cassette. Transcriptional and translational control sequences are DNA regulatory sequences, such as promoters, enhancers, polyadenylation signals, terminators, and the like, that provide for the expression of a coding sequence in a host cell.

A nucleic acid encoding a peptide extension of this invention is "operably linked" to the protein coding region when it is in an appropriate position relative to the coding sequence so as to enable increased expression of the coding sequence in a chloroplast. Typically, in a genetic construct of this invention, the nucleotides encoding the peptide extension are located upstream of the protein coding sequence. The two sequences may be fused in frame directly, or indirectly, via a linker sequence.

The terms "promoter", "promoter region" or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

An "inducible promoter" is a promoter which initiates transcription only when the plant is exposed to some particular external stimulus, as distinguished from constitutive promoters or promoters specific to a specific tissue or organ or stage of development. Although inducible plastid promoters are not currently available, it may be feasible to couple an inducible nuclear promoter to plastid expression through a system like the T7 polymerase system described by McBride et al., 1994, Proc. Natl. Acad. Sci. USA 91: 7301-7305. Briefly, in this system, an inducible nuclear promoter regulates the synthesis of chloroplast-targeted T7 polymerase, which, in turn, acts on recombinant plastid genes placed under T7 control.

Particularly preferred for the present invention are chemically-inducible promoters and wound-inducible promoters. Chemically inducible promoters include plant-derived promoters, such as the promoters in the systemic acquired resistance pathway, for example the PR promoters, e.g., the PR-1, PR-2, PR-3, PR4, and PR-5 promoters, especially the tobacco PR-1 a promoter and the *Arabidopsis* PR-1 promoter, which initiate transcription when the plant is exposed to BTH and related chemicals. See U.S. Pat. No. 5,614,395, incorporated herein by reference, and U.S. Provisional Application No. 60/027,228, incorporated herein by reference. Chemically-inducible promoters also include receptor-mediated systems, e.g., those derived from other organisms, such as steroid-dependent gene expression, copper-dependent gene expression, tetracycline-dependent gene expression, and particularly the expression system utilizing the USP receptor from *Drosophila* mediated by juvenile growth hormone and its agonists, described in PCT/EP96/04224, incorporated herein by reference, as well as systems utilizing combinations of receptors, e.g., as described in PCT/EP96/00686, incorporated herein by reference. Wound inducible promoters include promoters for proteinase inhibitors, e.g., the proteinase inhibitor II promoter from potato, and other plant-derived promoters involved in the wound response pathway, such as promoters for polyphenyl oxidases, LAP and TD. See generally, C. Gatz, "Chemical Control of Gene Expression", Annu. Rev. Plant Physiol. Plant Mol. Biol. (1997) 48: 89-108, the contents of which are incorporated herein by reference.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication.

A polynucleotide "exogenous to" an individual plant is a polynucleotide which is introduced into the plant, or a predecessor generation of the plant, by any means other than by a sexual cross. Examples of means by which this can be accomplished are described below, and include *Agrobacterium*-mediated transformation, biolistic methods, electroporation, in planta techniques, and the like.

"Increased expression" or "enhanced expression" of a polypeptide or protein of the present invention," or "increased expression" or "enhanced expression" of a polynucleotide encoding a polypeptide or protein of the present invention, refers to an augmented change in activity of the polypeptide or protein. Examples of such increased activity or expression include the following: (1) Activity of the protein or expression of the gene encoding the protein is increased above the level of that in wild-type, non-transgenic control plants; (2) Activity of the protein or expression of the gene encoding the protein is in an organ, tissue or cell where it is not normally detected in wild-type, non-transgenic control plants (i.e., spatial distribution of the protein or expression of the gene encoding the protein is altered); (3) Activity of the protein or expression of the gene encoding the protein is increased when activity of the protein or expression of the gene encoding the protein is present in an organ, tissue or cell for a longer period than in a wild-type, non-transgenic controls (i.e., duration of activity of the protein or expression of the gene encoding the protein is increased).

"Decreased expression or activity of a protein or polypeptide of the present invention," or "decreased expression or activity of a nucleic acid or polynucleotide encoding a protein of the present invention," refers to a decrease in activity of the protein. An example of such decreased activity or expression includes the decrease in activity of the protein or expression of the gene encoding the protein below the level of that in wild-type, non-transgenic control plants.

An "expression cassette" or a "recombinant expression cassette" refers to a nucleic acid construct, which when introduced into a host cell, results in transcription and/or translation of a RNA or polypeptide, respectively. Expression cassettes can be derived from a variety of sources depending on the host cell to be used for expression. For example, an expression cassette can contain components derived from a viral, bacterial, insect, plant, or mammalian source. In the case of both expression of transgenes and inhibition of endogenous genes (e.g., by antisense, or sense suppression) one of skill will recognize that the inserted polynucleotide sequence need not be identical and can be "substantially identical" to a sequence of the gene from which it was derived. A "plastid expression cassette" is an expression cassette which is integrated into the plastid DNA of the host.

The terms "isolated," "purified," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated nucleic acid of the present invention is separated from open reading frames (ORFs) that flank the desired gene and encode proteins other than the desired protein. The term "purified" denotes that a nucleic acid or protein gives rise to essentially one band in an electrophoretic gel. Particularly, it means that the nucleic acid or protein is at least 85% pure, more preferably at least 95% pure, and most preferably at least 99% pure.

"Homoplastidic" refers to a plant, plant tissue or plant cell wherein all of the plastids are genetically identical. This is the normal state in a plant when the plastids have not been transformed, mutated, or otherwise genetically altered. In different tissues or stages of development, the plastids may take different forms, e.g., chloroplasts, proplastids, etioplasts, amyloplasts, chromoplasts, and so forth.

In one aspect, the present invention addresses the need for a plentiful, inexpensive source of cellulose-degrading enzymes for such industries as the fuel ethanol production industry, cattle feed industry, and the paper and textile industries by replacing the conventional industrial cellulases produced by fungi with cellulases produced in plants. By genetically engineering plants to produce microbial cellulases, external application of cellulases for cellulose degradation will be unnecessary. For example, lignocellulosic biomass destined to become ethanol could serve as its own source of cellulase by utilizing the present invention. In fact, transgenic plants according to the present invention would not necessarily have to comprise all of the feedstock in a bioreactor; rather, they could be used in conjunction with non-transformed cellulosic feedstock, whereby the cellulases produced by the transgenic plants would degrade the cellulose of all the feedstock, including the non-transgenic feedstock. Cellulose degradation processes using transgenic biomass produced according to the present invention can be carried out more inexpensively, easily, and more environmentally safe than can conventional methods.

Enhanced expression in chloroplasts according to this invention may be combined with other known methods for chloroplast-targeted protein expression. Furthermore, the vectors of this invention may additionally include a DNA segment encoding a reporter gene, e.g. Green Fluorescent Protein (GFP).

Peptide Extension

A "peptide extension" refers to an amino acid sequence that is fused to a protein in frame, so that, when expressed in a plastid, the peptide extension enhances the expression of the protein that is fused in frame. The peptide extension may include any number of amino acids from an amino-terminus of a protein. The peptide extension may contain as few as two nucleic acids, and as many as fifty amino acids in length. In a preferred embodiment, the peptide extension is obtained from the amino terminus of a protein that is expressed in the chloroplast.

Preferably, the peptide extension is provided from a sequence encoding the amino acid chain known as an amino terminus (N-terminus) of a protein. In one embodiment of the present invention, the N-terminus of PsbA (D1), a photosystem II subunit (reaction center core protein of *Medicago sativa*), is used as a peptide extension. The peptide extension may encompass any number of the first 36 amino acids from the amino terminus of the PsbA protein of *M. sativa*; these 36 amino acids encompass the non-stromal portion of the mature PsbA protein (Kim J. et al., 2001, J. Biol. Chem. 266: 14931-14938). The peptide extension may encompass at least two contiguous amino acids, preferably at least ten contiguous amino acids, from the amino terminus of the PsbA protein of

*M. sativa*. The peptide extension needs to include contiguous amino acids from the amino terminus. These don't have to include the very beginning of the amino terminus. For example, a peptide extension may encompass five amino acids beginning with amino acid 3 from the N-terminus of PsbA, thereby encompassing amino acids No. 3 through No. 7.

Shown in SEQ ID NO:2 is the most preferred embodiment of the invention, which is a peptide extension encompassing the first 10 amino acids from the PsbA protein of *Medicago sativa* (amino acids No. 1 through No. 10). The peptide extension is fused to a sequence coding a desired protein. This fusion (genetic construct) is then introduced into the plastid genome, where it increases the expression of the desired protein that is fused with peptide extension.

An identical peptide extension for practicing the invention can also be isolated from the related plant *Medicago truncatula*. In another embodiment, a codon-optimized amino-terminal sequence obtained from the N-terminus of the psbA gene is used in a protein fusion construct. A skilled artisan might use other highly expressed chloroplast genes as starting points for generation of peptide extensions according to this invention. For example, peptide extensions encoded by the rbcL gene (Morton B. R., 1998, J. Mol. Evol. 46: 449-459) might be used in certain embodiments of this invention, for purposes of enhancing translation in the chloroplast.

In other aspects, the peptide extension of the present invention comprises a functional homolog of the peptide extension, i.e., the N-terminus sequence from the PsbA protein of *Medicago sativa*. A "functional equivalent" or "functional homolog" of a peptide of the present invention is a peptide that is homologous to the specified peptide but has one or more amino acid differences from the specified peptide. A functional fragment or equivalent of a peptide retains at least some, if not all, of the protein expression enhancing activity of the specified peptide.

A peptide extension functional homolog that preserves the peptide extension-like function includes any homolog in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the amino acid substitution is a conservative substitution. Conservative substitutions whereby an amino acid of one class is replaced with another amino acid of the same type fall within the scope of the invention so long as the substitution does not materially alter the biological activity of the compound.

A functional equivalent of SEQ ID NO:2 shares the same amino acid sequence as SEQ ID NO:2 except for a few amino acid differences, e.g., substitutions, insertions, or deletions. Thus, in certain embodiments, the peptide extension is substantially identical or substantially similar to the N-terminus-encoding sequence from the psbA gene of *Medicago sativa*. When expressed in a plant, both SEQ ID NO:2 and its functional homolog are expected to confer enhanced expression of a fused protein in the chloroplasts. For example, in the N-terminus of the PsbA protein of tobacco and barley, amino acid number 9 is glutamic acid (E), as opposed to aspartic acid (D). However, the change of E to D is relatively conservative and probably has minimal significance for the peptide extension function according to this invention. Therefore, in one embodiment, the peptide extension is obtained from the N-terminus of a PsbA protein obtained from any Fabaceae plant. In yet another embodiment, the peptide extension is obtained from the N-terminus of a PsbA protein obtained from any dicotyledonous plant.

Isolation of Nucleic Acids of the Present Invention

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., 1989, Molecular Cloning—A Laboratory Manual, Cold Spring Harbor Laboratory, Cold Spring Harbor, N.Y., or according to Ausubel et al., 1993, Current Protocols in Molecular Biology, Volumes 1-3, John Wiley & Sons, Inc.; Kriegler, 1990, Gene transfer and expression: A laboratory manual, Stockton Press, New York, each of which is incorporated herein by reference in its entirety.

The genes or nucleic acid sequences encoding proteins of the present invention includes genes and gene products identified and characterized by analysis using the nucleic acid sequences, including SEQ ID NO:1 and peptide, polypeptide, or protein sequences, including SEQ ID NO:2. Sequences encoding proteins of the present invention include nucleic acid sequences having substantial identity to SEQ ID NO:1. Indeed, shown in SEQ ID NO:1 are the first thirty nucleotides encoding PsbA from *M. sativa*. Peptide extensions of the present invention include peptides having substantial identity to SEQ ID NO:2.

The isolation of sequences from the genes used in the methods of the present invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form concatemers that can be packaged into the appropriate vector.

The cDNA or genomic library can then be screened using a probe based upon the sequence of a cloned gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology can be used to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes.

Appropriate primers and probes for identifying genes encoding a protein of the present invention from plant tissues are generated from comparisons of the sequences provided herein. For a general overview of PCR see Bartlett J. M. S., Stirling D., eds., 2003, PCR Protocols: Methods in Molecular Biology, second ed., Humana Press, Totowa, N.J. For examples of primers used see Examples section below.

Polynucleotides may also be synthesized by well-known techniques as described in the technical literature (Adams S.

P. et al., 1983, J. Am. Chem. Soc. 105: 661-663). Double-stranded DNA fragments may then be obtained either by synthesizing the complementary strand and annealing the strands together under appropriate conditions, or by adding the complementary strand using DNA polymerase with an appropriate primer sequence.

One useful method to produce the nucleic acids of the present invention is to isolate and modify the nucleic acid sequences of the present invention. Methods of sequence-specific mutagenesis of a nucleic acid are known. In addition, Ausubel et al., 1993, describe oligonucleotide-directed mutagenesis as well as directed mutagenesis of nucleic acids using PCR. Such methods are useful to insert specific codon changes in the nucleic acids of the invention.

Once a nucleic acid is isolated using the method described above, standard methods can be used to determine if the nucleic acid is a preferred nucleic acid of the present invention and therefore encodes a preferred protein of the present invention, e.g., by using structural and functional assays known in the art. For example, using standard methods, the skilled practitioner can compare the sequence of a putative nucleic acid sequence thought to encode a preferred protein of the present invention to a nucleic acid sequence encoding a preferred protein of the present invention to determine if the putative nucleic acid is a preferred polynucleotide of the present invention.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. One of skill will recognize that these values can be appropriately adjusted to determine corresponding identity of proteins encoded by two nucleotide sequences by taking into account codon degeneracy, amino acid similarity, reading frame positioning and the like. In some embodiments, polynucleotides of the present invention include nucleic acid sequences that have substantial identity to SEQ ID NO:1.

"Substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%. In some embodiments, polypeptides or proteins of the present invention include amino acid sequences that have substantial identity to SEQ ID NO:2.

Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine. Accordingly, polynucleotides of the present invention encoding a protein of the present invention include nucleic acid sequences that have substantial identity to the nucleic acid sequence of SEQ ID NO:1. In some embodiments, polypeptides or proteins of the present invention include amino acid sequences that have substantial similarity to SEQ ID NO:2.

Enhanced Expression of Heterologous Proteins

The term "genetic construct", "nucleic acid construct", or "DNA construct", is sometimes used to refer to a coding sequence or sequences inserted into an expression cassette for transforming a cell. The genetic construct may be operably linked to appropriate regulatory sequences and as such inserted into an expression cassette for transforming a cell. This term may be used interchangeably with the term "transforming DNA" or "transgene". The nucleic acid construct may contain a coding sequence for a gene product of interest, which may be fused to a sequence that enhances transcription of the gene product of interest. In addition, such a nucleic acid construct may contain a selectable marker gene and/or a reporter gene.

The term "selectable marker gene" refers to a gene encoding a product that, when expressed, confers a selectable phenotype such as antibiotic resistance on a transformed cell.

The term "reporter gene" refers to a gene that encodes a product which is easily detectable by standard methods, either directly or indirectly.

A "heterologous" region of a nucleic acid construct is an identifiable segment (or segments) of the nucleic acid molecule within a larger molecule that is not found in association with the larger molecule in nature. Thus, when the heterologous region encodes a plant gene, the gene will usually be flanked by DNA that does not flank the plant genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. Foreign, additional and/or modified versions of native or endogenous genes are referred to herein collectively as "transgenes".

The present invention provides methods of enhancing transgene expression in a plastid. In one embodiment of the invention, transgene expression is enhanced by creating a genetic construct including the polynucleotide of SEQ ID NO:1. The polynucleotide of SEQ ID NO:1 is fused in-frame to a heterologous protein, to create a fusion protein or polypeptide that will be expressed in chloroplasts. Accordingly, preferred nucleic acid sequences that encode peptide extensions for enhancing gene expression in plastids should have substantial identity to the coding region of SEQ ID NO:1, e.g., preferably at least 70%, at least 80%, or at least 95%, 96%, 97%, 98%, 99%, or 100% identity to the coding regions of SEQ ID NO:1.

Similarly, the preferred peptide extensions for enhancing gene expression in plastids should have substantial identity to the peptide of SEQ ID NO:2, e.g., preferably at least 70%, at least 80%, or at least 95%, 96%, 97%, 98%, 99%, or 100% identity to the peptide of SEQ ID NO:2.

One of skill will recognize that the polypeptides encoded by the genes of the invention, like other proteins, have different domains which perform different functions. Thus, the gene sequences need not be full length, so long as the desired functional domain of the protein is expressed.

One of skill will also recognize that the nucleotide sequence encoding the peptide extension may be linked to the protein-coding sequence via a linker sequence. The linker sequence can have variable length, so long as the peptide extension and the protein remain fused in a frame (Open Reading Frame), thereby creating a fusion protein.

If desired, the cellulase genes described in this application can be modified for expression in transgenic plant hosts. For example, the transgenic expression in plants of genes derived from microbial sources may require the modification of those genes to achieve and optimize their expression in plants. Bacterial open reading frames (ORFs) that encode separate enzymes but which are encoded by the same transcript in the native microbe are best expressed in plants on separate transcripts. To achieve this, each microbial ORF is isolated individually and cloned as fusion proteins or polypeptides within a recombinant cassette which provides a PsbA amino-terminal sequence at the 5' end of the ORF and a plant transcriptional terminator at the 3' end of the ORF. The isolated ORF sequence preferably includes the initiating ATG codon and the terminating STOP codon but may include additional sequence beyond the initiating ATG and the STOP codon. In addition, the ORF may be truncated, but still retain the required activity; for particularly long ORFs, truncated versions which retain activity may be preferable for expression in transgenic organisms. "Plant transcriptional terminator" is a transcriptional terminator that operates within plant cells.

The expression of genes derived from microbial sources may provide problems in expression. These problems have been well characterized in the art and can be dealt with according to standard methods known in the art. Typical problems include: (a) codon usage; (b) GC/AT content; and (c) sequences adjacent to the initiating methionine.

Preparation of Recombinant Vectors

The term "recombinant" when used with reference, e.g., to a cell, or nucleic acid, protein, expression cassette, or vector, indicates that the cell, nucleic acid, protein, expression cassette, or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "recombinant host cell" (or simply "host cell") refers to a cell into which a recombinant expression vector has been introduced. The phrase "host cell" refers to a cell from any organism. Preferred host cells are derived from plants, bacteria, yeast, fungi, insects or other animals. Methods for introducing polynucleotide sequences into various types of host cells are well known in the art. It should be understood that the term "host cell" is intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "vector" is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The present invention also provides vectors that contain recombinant expression cassettes comprising a promoter sequence operably linked to the genetic construct of the present invention. In some embodiments, the genetic construct comprises a polynucleotide sequence at least 80% identical to a polynucleotide sequence as shown in SEQ ID NO:1. The polynucleotide sequence is linked to nucleic acid encoding a heterologous protein so as to create a fusion protein. Using known genetic engineering techniques, the fusion protein is then inserted into a vector that it suitable for transformation of plants, and more preferably, into a vector that is suitable for transformation of plastids.

In some embodiments, the present invention provides host cells or progeny of host cells transformed with vectors including the recombinant expression cassettes of the present invention. In one aspect of the present invention, the host cell is a plant cell.

Various vectors are publicly available. The vector may, for example, be in the form of a plasmid, cosmid, viral particle, or phage. The appropriate nucleic acid sequence may be inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Construction of suitable vectors containing one or more of these components employs standard ligation techniques which are known to the skilled artisan.

To use isolated sequences in the above techniques, recombinant DNA vectors suitable for transformation of plastids are prepared. Techniques for transforming a wide variety of higher plant species are well known and described in the technical and scientific literature (Yoshida K. and Shinmyo A., 2000, J. Bioscience and Bioengineering 90: 353-362; Lessard P. A. et al., 2002, Metabolic Engineering 4: 67-79; Segal D. J. et al., 2003, Curr. Opin. Plant Biol. 6: 163-168). A DNA sequence coding for the desired polypeptide, for example a cDNA sequence encoding a full length protein, will preferably be combined with the peptide extension described above. The polynucleotide encoding the peptide extension and the polynucleotide coding for the desired polypeptide need to be linked in way that will ensure in-frame translation, i.e., synthesis of a translational fusion protein or polypeptide that will include the N-terminal peptide extension, and the desired protein. Additionally, this genetic construct may be combined with transcriptional and translational initiation regulatory sequences.

The vector comprising the sequences (e.g., promoters or coding regions) from genes of the invention might comprise a marker gene that confers a selectable phenotype on plant cells. For example, the marker may encode biocide resistance, particularly antibiotic resistance, such as resistance to spectinomycin, kanamycin, G418, bleomycin, hygromycin, or herbicide resistance, such as resistance to chlorosulfuron or Basta.

Plastid Transformation

Plastid transformation technology is described in U.S. Pat. Nos. 5,451,513, 5,545,817, and 5,545,818, all of which are hereby expressly incorporated by reference in their entireties. Plastid transformation is also described in McBride et al., 1994, Proc. Natl. Acad. Sci. USA 91: 7301-7305; Britt and May, 2003, Trends in Plant Science 8: 90-95; and in Bock et al., 2004, Trends in Biotechnology 6: 311-318, all of which are hereby incorporated by reference in their entireties. The basic technique for chloroplast transformation involves introducing regions of cloned plastid DNA flanking a selectable marker together with the gene of interest into a suitable target tissue, e.g., using biolistics or protoplast transformation. The 1 to 2 kb flanking regions, termed targeting sequences, facilitate homologous recombination with the plastid genome and thus allow the replacement or modification of specific regions of the plastome.

Initially, point mutations in the chloroplast 16S rRNA and rps12 genes conferring resistance to spectinomycin and/or streptomycin were utilized as selectable markers for transformation (Svab Z. et al., 1990, Proc. Natl. Acad. Sci. USA 87: 8526-8530, hereby incorporated by reference; Staub J. M., and Maliga P., 1992, Plant Cell 4: 39-45, hereby incorporated by reference). This resulted in stable homoplasmic transformants at a frequency of approximately one per 100 bombardments of target leaves. The presence of cloning sites between these markers allowed creation of a plastid targeting vector for introduction of foreign genes (Staub J. M. and Maliga P. 1993, EMBO J. 12: 601-606, hereby incorporated by reference). Substantial increases in transformation frequency were obtained by replacement of the recessive rRNA genes with a dominant selectable marker, the bacterial aadA gene encoding the spectinomycin-detoxifying enzyme aminoglycoside-3'-adenyltransferase (Svab Z. and Maliga P., 1993, Proc. Natl. Acad. Sci. USA 90: 913-917, incorporated herein by reference). Previously, this marker had been used successfully for high-frequency transformation of the plastid genome of the green alga *Chlamydomonas reinhardtii* (Goldschmidt-Clermont M., 1991, Nucl. Acids Res. 19: 4083-4089, incorporated herein by reference). Other selectable markers useful for plastid transformation are known in the art and encompassed within the scope of the invention. Typically, approximately 15-20 cell division cycles following transformation are required to reach a homoplasmic state.

The genetic constructs of the present invention may be introduced into any suitable plant tissue containing plastids. As used in conjunction with the present invention, the term "plant tissue" includes, but is not limited to, whole plants, plant cells, plant organs, plant seeds, protoplasts, callus, cell cultures, and any groups of plant cells organized into structural and/or functional units. Plants transformed in accordance with the present invention may be monocots or dicots and include, but are not limited to, maize, wheat, barley, rye, sweet potato, bean, pea, chicory, lettuce, cabbage, cauliflower, broccoli, turnip, radish, spinach, asparagus, onion, garlic, pepper, celery, squash, pumpkin, hemp, zucchini, apple, pear, quince, melon, plum, cherry, peach, nectarine, apricot, strawberry, grape, raspberry, blackberry, pineapple, avocado, papaya, mango, banana, soybean, tomato, sorghum, sugarcane, sugar beet, sunflower, rapeseed, clover, tobacco, carrot, cotton, alfalfa, rice, potato, eggplant, cucumber, *Arabidopsis*, and woody plants such as coniferous and deciduous trees.

Once a desired gene has been transformed into a particular plant species, it may be propagated in that species or moved into other varieties of the same species, particularly including commercial varieties, using traditional breeding techniques. Alternatively, the coding sequence for a desired protein, e.g., a cellulose-degrading enzyme, may be isolated, genetically engineered for optimal expression and then transformed into the desired plant variety.

The nucleic acids of the invention can be used to confer enhanced heterologous protein expression in essentially any plant. Thus, the invention has use over a broad range of plants, monocots and dicots, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna,* and *Zea*. Examples include tobacco and *Arabidopsis*, cereal crops such as maize, wheat, rice, soybean barley, rye, oats, sorghum, forage crops like alfalfa, barrel medic, clover and the like, oil-producing plants such as canola, safflower, sunflower, peanut and the like, vegetable crops such as tomato tomatillo, potato, pepper, eggplant, sugar beet, carrot, cucumber, lettuce, pea and the like, horticultural plants such as aster, begonia, chrysanthemum, delphinium, zinnia, lawn and turfgrasses and the like.

In one aspect, the invention is directed toward transformation of plastids in plants used for feedstock. The feedstock could be any type of lignocellulosic material such as high-biomass plants grown specifically for use as a source of biomass or waste portions of plants grown primarily for other purposes, such as stems and leaves of crop plants. Plants transformed with cellulase genes may be transformed with constructs that provide constitutive expression of cellulases if the particular plants can survive their own production of cellulases. If a particular type of plant experiences undue toxicity problems from the constitutive expression of cellulases, then the plant is preferably transformed with constructs that allow cellulase production only when desired. For example, with chemically inducible cellulase constructs, cellulase expression is chemically induced just before harvesting plants so that just as the plants are being killed by their own production of cellulases, they are harvested anyway. Plant tissue is then crushed, ground, or chopped to release the cellulases then added to a bioreactor in which the lignocellulosic biomass would be degraded into simple sugars by the action of the cellulases expressed in the transgenic plants.

Plant Analysis

The term "plant" includes whole plants, shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, bryophytes, and multicellular algae. It includes plants of a variety of ploidy levels, including aneuploid, polyploid, diploid, haploid and hemizygous.

The present invention also provides transgenic plants. In one aspect of the present invention, transgenic plants of the present invention comprise recombinant expression cassettes of the present invention. In one embodiment of the present invention, the transgenic plant has enhanced heterologous protein expression in chloroplasts. In one aspect, the heterologous protein is a cellulase.

Using known procedures, one of skill can screen for plants of the invention by detecting increased or decreased levels of the claimed gene and claimed protein in a plant and detecting the desired phenotype. Means for detecting and quantifying mRNA or proteins are well known in the art. Gene expression can be measured in a sample directly, for example, by Northern blotting to quantitate the transcription of mRNA, dot blotting (DNA analysis), DNA microarrays, or in situ hybridization, using an appropriately labeled probe, based on the sequences provided herein. Various labels can be employed, most commonly radioisotopes, particularly $^{32}P$. However, other techniques can also be employed, such as using biotin-modified nucleotides for introduction into a polynucleotide. The biotin then serves as the site for binding to avidin or antibodies, which can be labeled with a wide variety of labels, such as radionuclides, fluorophores, enzymes, or the like.

"Cellulose-degrading enzymes" described herein include cellulases, cellobiohydrolases, cellobioses, and other enzymes involved in breaking down cellulose and hemicellulose into simple sugars such as glucose and xylose. Preferably, the cellulose-degrading enzymes used in the present invention are of non-plant origin. The cellulose-degrading enzymes are preferably of microbial origin, more preferably of bacterial origin, for example from a bacteria of the genus *Thermomonospora*, e.g., from *Thermomonospora fusca*. Explicitly, but not exclusively, included within the term cellulose-degrading enzymes are those enzymes that fall under the Enzyme Classification heading EC 3.2.1.x. A non-exhaustive list of these enzymes, the genes for all of which can be used in the present invention, includes Table in U.S. Pat. No. 5,981,835, the Table I being incorporated herein in its entirety by reference.

The activity of cellulose-degrading enzymes in transplastomic plants can be assayed using methods known in the art, e.g., cellulose assays described in U.S. Pat. No. 6,818,803, herein incorporated by reference. Some of these methods are also described in the Examples section below.

In one aspect of the invention, transplastomic cellulose-degrading enzyme-expressing plants may be crossed with of nuclear-transformed cellulose-degrading enzyme-expressing plants. Through breeding, it would be possible to produce a doubly-transformed plant that expresses at high levels two types of cellulose-degrading enzymes, e.g., both cellobiohydrolase and endoglucanase with a preponderance of the enzyme expressed in the chloroplasts. Such breeding approach can be particularly successful in plants that have maternal inheritance of the plastidic genome (e.g., tobacco). Based on studies of purified cellulases, such doubly-transformed plants, expressing two types of cellulases, might exhibit a synergistic increase in enzymatic activity.

Examples

The invention will be further described by reference to the following detailed examples. These examples are provided for purposes of illustration only, and are not intended to limit the claimed invention.

Identification of the Peptide Extension for Enhanced Expression in Chloroplasts:

Two versions of a microbial cellulase open reading frame (ORF) were tested. As a control, a "wild type" ORF encoding a polypeptide differing from the native enzyme only in the addition of a single methionine at the N-terminus was used. In accordance with the invention, a modified ORF (nORF) consisting of the first thirty nucleotides of the PsbA coding sequence (SEQ ID NO:1) was fused to the above sequence. In other words, nORF was a genetic construct that encoded the peptide extension fused in frame to the microbial cellulase. In separate transformation experiments, both constructs (control ORF and modified nORF) were introduced into the plastid genome as tandem insertions with the bacterial aadA for conferring spectinomycin resistance. Insertion was targeted to the ribosomal RNA operon, between trnI and trnA, with expression of the transgenes driven by the endogenous ribosomal operon promoter (Prm).

Analysis of expression levels indicated that the novel ORF construct (nORF) yielded 50- to 100-fold higher levels of cellulase activity than the "wild type" ORF (see FIG. 1). Thus, the addition of the peptide extension of this invention to a microbial cellulase resulted in significantly enhanced expression of the fusion protein in chloroplasts.

Vector Construction

An existing vector directing intracellular accumulation of cellulase was used as a template for PCR-amplification of the ORF (Ziegelhoffer et al., 2001, Mol. Breeding 8:147-158). A novel Nco I site was introduced at the 5' end (5'-ccatg-gcgggcggcggctattg-3'; SEQ ID NO:3), facilitating subsequent cloning steps. The 3' end of the ORF incorporates a Sac I site (5'-tggagctctagacaggatcgaaaat-3') and includes coding sequence up to the GTC codon specifying valine 358. To the 5' end of the ORF was added the 5' UTR of bacteriophage T7 gene 10. This sequence was obtained from the pET14b vector (Novagen) as a Xba I to Nco I fragment. The 3' end of the ORF was fused to the 3' UTR of psbA from *Medicago sativa* to yield a promoterless expression cassette. This sequence was amplified from *M. sativa* genomic DNA (RSY27) using the primers psbASac (5'-gagctcggtttaaaaaaaggatacga-3'; SEQ ID NO:4) and psbAAcc (5'-gtatacagaaaaagactacta-3'; SEQ ID NO:5). Importantly, the *M. sativa* psbA 3' UTR shows no detectable sequence homology to the relatively widely-used *N. tabacum* psbA 3' UTR. The cellulase expression cassette was obtained by further modification to include the oligonucleotide shown in SEQ ID NO:1.

Ligation of this oligonucleotide to Nco I-cut vector in the correct orientation destroyed the Nco I site overlapping the start codon and created an in-frame fusion coding for a product in which the N-terminal 10 amino acids of *M. sativa* PsbA precede the cellulase sequence. The correct orientation of the '10N-psbA' sequence was confirmed by PCR.

The selectable marker aadA, encoding spectinomycin resistance, was assembled in a similar manner. Primers Sal1aadA (5'-gagtcgaccatggcggaagcggtgatcgccgaa-3'; SEQ ID NO:6) and Sac1aadA (5'-tggagctcttatttgccgactaccttggt-3'; SEQ ID NO:7) were used to amplify the aadA ORF present in pPZP211 (NCBI accession #U10490). To this sequence were added the 5' and 3' UTRs described above.

Targeting of the tandem expression cassettes to the trnI-trnA intergenic region was facilitated by vector pP3.27-1, comprising approximately 3.8 kilobases of tobacco plastid DNA (cpDNA) spanning the 3' end of the 16S rRNA gene and the 5' end of the 23S rRNA gene. Primers tob16S (5'aagaatgaaactcaaaggaattg-3'; SEQ ID NO:8) and tob23S (5'gtcatatctagtattcagagttt-3'; SEQ ID NO:9) were used to amplify this region from Petite Havana genomic DNA. The PCR product was cloned into pSTBlue-1 (Novagen) and sequenced to ensure the absence of mutations. An Sph I site within the vector polylinker was removed by Kpn I digestion (releasing an ~80 bp fragment), followed by religation. The final targeting vector had a unique Sph I site between the trnI and trnA genes, facilitating the insertion of Sph I fragments containing the promoterless cassettes for cellulase and the aadA selectable marker. The final constructs (pP4.09-9, pP5.91-28) directed insertion (via homologous recombination) of both the cellulase and selectable marker cassettes into the ribosomal RNA (rrn) operon. This strategy allows us to take advantage of the strong, endogenous rrn promoter to drive expression of both genes, with the benefit that expression is low or non-existent in intermediary vectors due to the absence of promoter sequences.

Plant Transformation

Transformation vectors were introduced into tobacco leaf explants by biolistic transformation, essentially as described earlier (Svab Z. et al 1990, Svab Z. and Maliga P., 1993). Leaf explants were removed from plants grown in vitro and placed adaxial side up on RMOP medium (MS salts, N6-benzyladenine [1 mg/l], 1-naphthaleneacetic acid [0.1 mg/l], thiamine [1 mg/l], inositol [100 mg/l], agar [6 g/l], sucrose [30 g/l], pH adjusted to 5.8). Bombardment with DNA-coated 1.0 µm tungsten particles was carried out at a pressure of 6.2 MPa (900 psi) and a target distance of 6 cm using a BioRad PDS 1000 He instrument. Immediately after bombardment, plates were placed in a plant growth incubator under 4 layers of cheesecloth ("low light"). Two days after bombardment, the explants were cut into smaller pieces (<1 cm$^2$) and placed on RMOP medium containing 500 mg/L spectinomycin. During this time, explants were maintained under reduced light (30 µE). Shoots were removed to fresh RMOP containing spectinomycin and rooted on MST medium. Plastid transformants were subjected to two additional rounds of shoot regeneration under spectinomycin selection.

Plant Analysis

Spectinomycin-resistant shoots were sampled for DNA analysis as soon as they were of sufficient size. Sampling continued at intervals through cycles of regeneration. Tobacco genomic DNA was prepared by the method of Fulton et al., 1995, Plant Mol. Biol. Rep. 13: 207-209.

Confirmed plant transformants were sampled for enzyme activity. Leaf samples were homogenized in grinding buffer (50 mM NaOAc, pH 5.5, 100 mM NaCl, 10% (v/v) glycerol, 0.5 mM ethylenediaminetetraacetic acid (disodium salt), 1 mM phenylmethylsulfonyl fluoride) at a ratio of 5-10 µl per mg of sample (fresh weight). Samples were homogenized with a power drill using 1.5 ml microcentrifuge tubes and plastic pestles. Soluble extract was recovered from insoluble debris after centrifugation at 15,000×g for 5 min. The protein concentration of extracts was determined using the BioRad protein assay and normalized to the supplied BSA standard.

Appropriate dilutions of plant extracts were assayed for cellulase activity using a 96-well plate format. The reaction buffer contained 50 mM NaOAc pH 5.5, 100 mM NaCl, 0.5 mM 4-methylumbelliferyl β-D-cellobioside (MUCB). MUCB hydrolysis by the enzyme releases the fluorescent product, 4-methylumbelliferone ($\lambda$ex=360 nm, $\lambda$em=465 nm). Each well contained 1 µl of the sample to be assayed and 100 µL reaction buffer. Extracts were diluted up to 100-fold to obtain values within the linear range of the assay. Plates were covered with adhesive lids to prevent evaporation and incubated for 30 min at 65° C. The reaction was terminated by the addition of 100 µl of stop mix (0.15 M glycine pH 10.0) and fluorescence was determined with a Tecan SPECTRAFluor Plus at 465 nm using an excitation wavelength of 360 nm. Fluorescence values were compared to values obtained with 12 to 240 picograms of purified cellulase, a range of enzyme concentrations that yields a linear response. A series of 4-methylumbelliferone standards (4 to 160 picomoles) was also included. For all transgenic plant samples, cellulase activity was determined by subtracting the background contributed by Petite Havana control extracts (done in parallel). All data collected represent the mean of duplicate determinations.

After the initial bombardment/regeneration cycle, plants showing the highest level of cellulase activity were subjected to another round of regeneration to yield "regen 2" plants. This process was repeated to yield a set of "regen 3" plants that were transferred to soil for subsequent selfing and seed production.

In a comparison of cellulase activity (FIG. 1), the nORF transformants yield 50- to 100-fold more activity than ORF (control) transformants. In FIG. 1, each data point represents the mean of the 4 highest-expressing plants in each group. The percent of total soluble protein is determined by relating the 4-methylumbelliferyl β-D-cellobioside (MUCB) hydrolysis activity of crude plant extracts to the activity of purified cellulase. Untransformed tobacco Petite Havana leaf extracts were used for background subtraction. A "wild type" cellulase encoding a polypeptide differing from the native enzyme only in the addition of a single methionine at the N-terminus (ORF) and a modified ORF (nORF) consisting of the first 30 nucleotides of the plastid PsbA-coding sequence fused to the above cellulose sequence.

For both constructs, the percent of total soluble protein (% TSP) increased with cycles of regeneration, reflecting the gradual replacement of wild-type cpDNA with recombinant cpDNA. The obtained recombinant cellulase is extraordinarily stable in crude plant extracts, with no loss of activity observed after 20 days at 28° C.

Because the ORF and nORF constructs are identical except for the 10 amino acid PsbA N-terminal extension present in the latter, this N-terminal extension probably functions to increase translation efficiency, protein folding, or both.

It is to be understood that this invention is not limited to the particular methodology, protocols, patients, or reagents described, and as such may vary. It is also to be understood that the terminology used herein is for the purpose of describing particular embodiments only, and is not intended to limit the scope of the present invention, which is limited only by the claims.

The invention having been fully described, it is preferably apparent to one skilled in the art that changes and modifications can be made thereto without departing from the spirit and scope thereof.

What is claimed is:

1. A genetic construct encoding a fusion protein, wherein the construct comprises:
   a) a first nucleic acid sequence encoding a peptide extension comprising (i) an amino acid sequence that is at least 90% identical to the amino acid sequence of SEQ ID NO:2 or (ii) an amino acid sequence of SEQ ID NO:2 having 1 conservative amino acid substitution; and
   b) a second nucleic acid sequence encoding a protein other than *Medicago sativa* PsbA;
   wherein the first nucleic acid sequence and the second nucleic acid sequence are operably linked so they read in frame; and
   wherein the peptide extension increases the expression of said protein in a plastid.

2. The genetic construct of claim 1, wherein the first nucleic acid sequence is at least 95% identical to the nucleic acid sequence of SEQ ID NO:1.

3. The genetic construct of claim 1, wherein the peptide extension comprises the first ten amino acids of a *Medicago sativa* PsbA protein or its homolog.

4. The genetic construct of claim 1, wherein the first nucleic acid sequence encodes the first 36 amino acids of the amino terminal sequence of a *Medicago sativa* PsbA protein.

5. The genetic construct of claim 1, wherein the expression of said protein in the plastid is at least 10 times greater than the expression of said protein alone.

6. The genetic construct of claim 1, wherein the second nucleic acid sequence encodes a heterologous protein.

7. The genetic construct of claim 1, wherein the first nucleic acid is linked to the second nucleic acid via a linker sequence.

8. The genetic construct of claim 1, further comprising a heterologous promoter sequence operatively linked to the genetic construct.

9. The genetic construct of claim 1, wherein the protein is a cellulose-degrading enzyme.

10. A recombinant expression cassette comprising the genetic construct of claim 1.

11. A plastid expressing the genetic construct of claim 1.

12. The plastid of claim 11, which is a chloroplast.

13. A vector comprising the recombinant expression cassette of claim 10.

14. A transgenic plant comprising the recombinant expression cassette of claim 10.

15. A recombinant host cell comprising the vector of claim 13.

16. A transgenic plant comprising the genetic construct of claim 1.

17. A method of increasing protein expression in a plastid, said method comprising introducing the genetic construct of claim 1 into the plastid, wherein the peptide extension increases the expression of said protein in the plastid.

18. The method of claim 17, wherein the first nucleic acid sequence encodes the first ten amino acids of a *Medicago sativa* PsbA protein.

19. The method of claim 17, wherein the plastid is a chloroplast.

20. A recombinant expression cassette comprising:
   a) a first polynucleotide encoding a peptide extension comprising (i) an amino acid sequence that is at least 90% identical to the amino acid sequence of SEQ ID NO:2 or (ii) an amino acid sequence of SEQ ID NO:2 having 1 conservative amino acid substitution; and
   b) a second polynucleotide encoding a cellulose-degrading enzyme;
   wherein the first polynucleotide and the second polynucleotide are operably linked so they read in frame; and
   wherein the peptide extension increases the expression of the cellulose-degrading enzyme in a plastid.

21. The recombinant expression cassette of claim 20, wherein the first polynucleotide is at least 95% identical to the nucleic acid sequence of SEQ ID NO:1.

22. The recombinant expression cassette of claim 20, wherein the first polynucleotide encodes the amino acid sequence of SEQ ID NO:2.

23. The recombinant expression cassette of claim 20, wherein the first nucleic acid sequence encodes the first 36 amino acids of the amino terminal sequence of a *Medicago sativa* PsbA protein.

* * * * *

UNITED STATES PATENT AND TRADEMARK OFFICE
CERTIFICATE OF CORRECTION

PATENT NO. : 7,745,698 B2
APPLICATION NO. : 11/600566
DATED : June 29, 2010
INVENTOR(S) : Thomas Ziegelhoffer and Sandra Austin-Phillips It is certified that error appears in the above-identified patent and that said Letters Patent is hereby corrected as shown below:

In column 4, line 46, change "PR-1 a" to --PR-1a--.

In column 7, line 67, change "fabaceae" to --*fabaceae*--.

In column 16, line 44, change 'Ito" to --I to--.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

PATENT NO. : 7,745,698 B2  
APPLICATION NO. : 11/600566  
DATED : June 29, 2010  
INVENTOR(S) : Thomas Ziegelhoffer et al.

Page 1 of 1

It is certified that error appears in the above-identified patent and that said Letters Patent is hereby corrected as shown below:

In the Specification

<u>Column 1, Lines 7-9:</u>
Delete the phrase:
"The development of the present invention was supported by USDA/ARS project funds. The U.S. Government may have certain rights in the invention described herein."

And replace with:
--This invention was made with government support under 2003-35504-12875 awarded by the USDA/NIFA. The government has certain rights in the invention.--.

Signed and Sealed this
Twenty-ninth Day of December, 2020

Andrei Iancu
*Director of the United States Patent and Trademark Office*

SEQUENCE LISTING

<160> NUMBER OF SEQ ID NOS: 9

<210> SEQ ID NO 1
<211> LENGTH: 30
<212> TYPE: DNA
<213> ORGANISM: Medicago sativa

<400> SEQUENCE: 1
atgactgcaa ttttagagag acgccatagc                                              30

<210> SEQ ID NO 2
<211> LENGTH: 10
<212> TYPE: PRT
<213> ORGANISM: Medicago sativa

<400> SEQUENCE: 2

Met Thr Ala Ile Leu Glu Arg Arg Asp Ser
1               5                   10

<210> SEQ ID NO 3
<211> LENGTH: 22
<212> TYPE: DNA
<213> ORGANISM: Artificial Sequence
<220> FEATURE:
<223> OTHER INFORMATION: Vector 5' end sequence with Nco I site

<400> SEQUENCE: 3
ccatggcggg cggcggctat tg                                                      22

<210> SEQ ID NO 4
<211> LENGTH: 26
<212> TYPE: DNA
<213> ORGANISM: Artificial Sequence
<220> FEATURE:
<223> OTHER INFORMATION: Primer sequence psbASac

<400> SEQUENCE: 4
gagctcggtt taaaaaaagg atacga                                                  26

<210> SEQ ID NO 5
<211> LENGTH: 21
<212> TYPE: DNA
<213> ORGANISM: Artificial Sequence
<220> FEATURE:
<223> OTHER INFORMATION: Primer sequence psbAAcc

<400> SEQUENCE: 5
gtatacagaa aaagactact a                                                       21

<210> SEQ ID NO 6
<211> LENGTH: 33
<212> TYPE: DNA
<213> ORGANISM: Artificial Sequence
<220> FEATURE:
<223> OTHER INFORMATION: Primer sequence Sal1aadA

<400> SEQUENCE: 6
gagtcgacca tggcggaagc ggtgatcgcc gaa                                           33

<210> SEQ ID NO 7
<211> LENGTH: 29
<212> TYPE: DNA
<213> ORGANISM: Artificial Sequence -continued

```
<220> FEATURE:
<223> OTHER INFORMATION: Primer sequence Sac1aadA

<400> SEQUENCE: 7
tggagctctt atttgccgac taccttggt                                    29

<210> SEQ ID NO 8
<211> LENGTH: 23
<212> TYPE: DNA
<213> ORGANISM: Artificial Sequence
<220> FEATURE:
<223> OTHER INFORMATION: Primer sequence tob16S

<400> SEQUENCE: 8
aagaatgaaa ctcaaaggaa ttg                                          23

<210> SEQ ID NO 9
<211> LENGTH: 23
<212> TYPE: DNA
<213> ORGANISM: Artificial Sequence
<220> FEATURE:
<223> OTHER INFORMATION: Primer sequence tob23S

<400> SEQUENCE: 9
gtcatatcta gtattcagag ttt                                          23
```